(12) United States Patent
Kitazumi et al.

(10) Patent No.: US 9,353,018 B2
(45) Date of Patent: May 31, 2016

(54) ORGANIC FERTILIZER PRODUCTION SYSTEM

(75) Inventors: Kazushige Kitazumi, Tokyo (JP); Yasuharu Nakano, Minato-ku (JP); Yaroslava Polutova, Minato-ku (JP); Koji Nagae, Minato-ku (JP); Ryoichi Sekiya, Minato-ku (JP); Hisaki Yamawaki, Minato-ku (JP)

(73) Assignee: E's Inc., Tokyo (JP)

( * ) Notice: Subject to any disclaimer, the term of this patent is extended or adjusted under 35 U.S.C. 154(b) by 27 days.

(21) Appl. No.: 14/113,476

(22) PCT Filed: Apr. 5, 2012

(86) PCT No.: PCT/JP2012/059312
§ 371 (c)(1),
(2), (4) Date: Jan. 6, 2014

(87) PCT Pub. No.: WO2012/147483
PCT Pub. Date: Nov. 1, 2012

(65) Prior Publication Data
US 2014/0123902 A1 May 8, 2014

(30) Foreign Application Priority Data
Apr. 28, 2011 (JP) ................................. 2011-100358

(51) Int. Cl.
*A01K 29/00* (2006.01)
*C05F 3/06* (2006.01)
(Continued)

(52) U.S. Cl.
CPC ................. *C05F 3/06* (2013.01); *A01K 67/033* (2013.01); *C05F 17/0009* (2013.01); *Y02P 20/145* (2015.11); *Y02W 30/43* (2015.05)

(58) Field of Classification Search
CPC ....... A01K 67/033; C05F 17/00; C05F 17/02; C05F 17/0009; C05F 3/06; C05F 9/02; C05F 3/00; C05F 9/00; C05F 9/04; Y02W 30/43

USPC .................. 119/6.5, 6.6, 6.7; 71/8, 9, 15, 21; 435/290.1, 290.4
See application file for complete search history.

(56) References Cited

U.S. PATENT DOCUMENTS 3,716,371 A * 2/1973 Calvert et al. ..................... 426/2
3,814,057 A * 6/1974 Calvert et al. .................. 119/6.6
(Continued)

FOREIGN PATENT DOCUMENTS

JP 2002-011440 A 1/2002
JP 2002-020190 A 1/2002
(Continued)

*Primary Examiner* — Trinh Nguyen
(74) *Attorney, Agent, or Firm* — Sughrue Mion, PLLC

(57) ABSTRACT

[Problem] To provide an efficient system for manufacturing an organic fertilizer base material that reduces the manual labor involved in treating livestock manure using *Musca domestica* larvae. [Solution] Provided is an organic fertilizer production system for producing organic fertilizer from the excreta of livestock by using the larvae of *Musca domestica*. The organic fertilizer production system is configured as follows: provided is a first cultivation processing housing unit for cultivating larvae hatched from eggs; disposed is a second cultivation processing housing unit that is divided into a plurality of sections below the first cultivation processing housing unit; provided is a drop part that allows the larvae to fall by utilizing the fact that the larvae crawl; an organic fertilizer base is manufactured by letting the larvae fall from the drop part into the next stage of the second cultivation processing housing unit and repeating this process several times, and in each of the cultivation processing housing units, the excreta is enzymatically hydrolyzed within the larvae during the process of rearing the larvae and is subsequently excreted by the larvae; provided are an organic fertilizer base gathering unit that gathers the produced organic fertilizer base material and discharges the same, and a larvae gathering unit that gathers the larvae group that crawled and fell from the final section of the cultivation processing housing unit; and the organic fertilizer base and the larvae group are discharged.

5 Claims, 9 Drawing Sheets

(51) Int. Cl.
    *A01K 67/033*    (2006.01)
    *C05F 17/00*    (2006.01)

(56)            References Cited

U.S. PATENT DOCUMENTS

| | | | | |
|---|---|---|---|---|
| 3,961,603 | A | * | 6/1976 | Gaddie, Sr. ................... 119/6.7 |
| 4,040,810 | A | * | 8/1977 | Eby et al. ............................ 71/9 |
| 4,262,633 | A | * | 4/1981 | Taboga .......................... 119/6.7 |
| 5,178,094 | A | * | 1/1993 | Carr et al. ....................... 119/6.5 |
| 5,351,643 | A | * | 10/1994 | Hughes ........................... 119/6.5 |
| 5,741,344 | A | * | 4/1998 | Warkentin ........................... 71/9 |
| 5,759,224 | A | * | 6/1998 | Olivier ................................. 71/9 |
| 6,001,146 | A | * | 12/1999 | Olivier ................................. 71/9 |
| 6,391,620 | B1 | * | 5/2002 | Olivier ....................... 435/262.5 |
| 6,474,259 | B1 | * | 11/2002 | Gaugler .......................... 119/6.7 |
| 7,998,728 | B2 | * | 8/2011 | Rhoads et al. ............. 435/290.1 |
| 2003/0143728 | A1 | * | 7/2003 | Olivier ....................... 435/290.1 |
| 2004/0089241 | A1 | * | 5/2004 | Zhang ............................ 119/6.5 |
| 2010/0129273 | A1 | * | 5/2010 | Milin ............................. 422/187 |
| 2010/0273251 | A1 | * | 10/2010 | Rhoads et al. ............. 435/290.1 |
| 2012/0214223 | A1 | * | 8/2012 | Hughes ....................... 435/287.1 |
| 2013/0206071 | A1 | * | 8/2013 | Caprio et al. .................. 119/6.5 |
| 2013/0319334 | A1 | * | 12/2013 | Newton et al. ................ 119/6.5 |

FOREIGN PATENT DOCUMENTS

| | | |
|---|---|---|
| JP | 2005-132683 A | 5/2005 |
| JP | 2010-110307 A | 5/2010 |
| JP | 2012-116664 A | 6/2012 |
| JP | 2012-116665 A | 6/2012 |

* cited by examiner

ORGANIC FERTILIZER PRODUCTION SYSTEM

This application is a National Stage of International Application No. PCT/JP2012/059312 filed Apr. 5, 2012, claiming priority based on Japanese Patent Application No. 2011-100358 filed Apr. 28, 2011, the contents of all of which are incorporated herein by reference in their entirety.

TECHNICAL FIELD

The present invention relates to a method for producing organic fertilizer from excreta of livestock by using *Musca domestica* (housefly) larvae.

BACKGROUND TECHNOLOGY

In livestock facilities such as pig firming and diary firming, excreta are discharged every day and an amount of excreta is generally proportional to a breeding number of animals. Usually, the excreta is composted by means of microorganisms Disposal of excreta by microorganisms, however, consume too long time because of higher percentage of liquid components in the excreta. In some areas, the livestock excreta generated in large quantities are left on ground without treatment, resulting in contamination of ground water, which has become a cause of social problems.

Therefore, how to dispose of excreta is a problem to be solved today. In particular, it is not allowed any more to damp unsanitary excreta which give off a bad smell due to the recent severe regulation for environmental protection.

An amount of excreta of livestock is increasing along with expansion of the livestock scale but it is not easy to dispose of excreta generated daily in a large quantity efficiently in a short period of time. Therefore, disposal of livestock excreta is a heavy burden for livestock farmers.

Under such situation, it was proposed to use an insect bio-processing system for processing animal excreta so as to reduce the above burden (see Patent Document 1).

The insects bio-processing system disclosed in Patent Document 1 comprises a means for conveying sequentially processing-containers on which animal excreta are placed, a means for preying animal excreta onto an empty processing-container conveyed successively, a means to depositing eggs or larvae of housefly into unfermented excreta in the processing containers, a means for maturing excreta for a require duration in the processing containers stacked in multiple stages, a means to collect larvae or pupa metamorphosed from the larvae of housefly crawling out of the processing-containers, and a means for recovering finished or matured excreta from the processing-container which is advanced successively.

In this insect bio-processing system, reduction of harm or detoxification of excreta can be realized by preying or feeding animal excreta to housefly.

PRIOR ARTS

Patent Documents

Patent Document 1: JP-A1-2002-11440

DISCLOSURE OF THE INVENTION

Problems to be Solved by the Invention

Reduction of harm or detoxification of excreta is done by preying or feeding animal excreta to housefly can be realized in this insect bio-processing system disclosed in Patent Document 1, however, a treatment or handling for producing organic fertilizer from housefly larvae must be carried out in a processing chamber whose temperature and humidity are adjustable. Still more, all of deposition of housefly eggs onto excreta placed in a container, of hatching of eggs, of growing of larvae, and loading and unloading of the containers must be done manually.

Moreover, larvae crawling out of the containers must be handled manually, since this method utilizes such a habit of housefly that larvae come out a medium to become pupae after larvae grow in certain level. However, working environment in the processing chamber to carry out the above works is extremely poor and is not amenable to manual labor, because the work environment is filled with odor of excreta and grown larvae (maggots) are crawling all around.

Still moreover, there is another problem. An amount of prey or feed processed by the larvae of houseflies increases explosively in a week when there is enough breeding volume and food. On the contrary, if such enough breeding volume and food are not available, an amount of organic fertilizer base material which is produced within the bodies of larvae by enzymatic decomposition and excreted out of larvae decrease and the growth of larvae become also slow.

The present invention was done in view of the above problems of prior arts. In the present invention, disposal of animal excreta such as pig feces effected by housefly larvae can be done under such condition that a sufficient nurturing area for larvae is available, that a sufficient amount of prey or feed can be supplied to larvae to accelerate the growth thereof, that an amount of excrete produced within the body of larva by enzymatic decomposition of livestock excreta can be increased and that manual handling operation in the processing storage room is not necessary.

Thus, the present invention provides a system which can produce organic fertilizer from animal excreta efficiently with less labor.

Means to Solve the Problems

In order to solve the above problems, an exemplary embodiment of the invention, in particular Example 1, is an organic fertilizer producing system for producing organic fertilizer from excreta of livestock or domestic animal by using larvae of *Musca domestica* (housefly), characterized in that a first nurturing-processing storage unit for nurturing or growing larvae hatched from eggs is provided, that a plurality of second nurturing-processing storage units is arranged below the first nurturing-processing storage unit, that the first nurturing-processing storage unit has a dropping part, so that grown larvae drop onto the second nurturing-processing storage units covered with excreta of livestock, by utilizing such a behavior of larvae that they crawl out of the first nurturing-processing storage unit, that a plurality of third nurturing-processing storage units are arranged below the second nurturing-processing storage units in the same way as above, so that grown larvae drop onto the third nurturing-processing storage units covered with excreta of livestock, that the above processing is reaped for required several times until the final nurturing-processing storage unit, wherein the excreta of livestock are decomposed with enzyme within larvae bodies during larvae are nurtured in each nurturing-processing storage unit, while the larvae excrete or produce an organic fertilizer base material, that a collecting section for collecting the organic fertilizer base material produced is provided, and that a larvae collecting section for collecting grown larvae crawling out of the final nurturing-processing storage unit is provided, the resulting collected larvae as well as the organic fertilizer base material produced being carried out of the system.

An exemplary embodiment of the invention corresponds to Examples 1 to 4, the organic fertilizer producing system, characterized in that each of the nurturing-processing storage comprises a dropping part and a receiving part for larvae on a fixed frame, and a bottom part on which a flat body is placed movably.

An exemplary embodiment of the invention corresponds mainly to Example 5, the organic fertilizer producing system, characterized in that each of the nurturing-processing storage unit comprises a series of movable trays each having a bottom part and a dropping part and a receiving part for the larvae, the trays being circulated by a conveyor.

An exemplary embodiment of the invention corresponds mainly to Examples 1 and 4, the organic fertilizer producing system, characterized in that each of the nurturing-processing storage unit has a receiving part located at a position corresponding to the dropping part of an upper nurturing-processing storage unit, the receiving part comprising a flat body in a form of a projection which projects outward and having a width equal to a width of the dropping part divided by a predetermined number.

An exemplary embodiment of the invention corresponds mainly to Example 2, the organic fertilizer producing system, characterized in that each of the nurturing-processing storage unit has a receiving part located at a position corresponding to the dropping part of an upper nurturing-processing storage unit, the receiving part comprising an edged roller having edges on its surface for hurting dropping larvae and having a width equal to a width of the dropping part divided by a predetermined number.

An exemplary embodiment of the invention corresponds mainly to Example 1, the organic fertilizer producing system, characterized in that the larvae collecting section has an imago extraction part for extracting a part of imagoes or a part of pupas grown, so that imagoes of houseflies extracted in the imago extraction part and are is guided though a duct to an egg depositing-hatching unit located above the first nurturing-processing storage unit.

An exemplary embodiment of the invention corresponds mainly to Example 1, the organic fertilizer producing system, characterized in that a plurality of rotary chambers are arranged in the egg depositing-hatching unit and a prey is fed into one of the chambers whose opening is directed upwards, while the prey is irradiated with ultraviolet rays, so that imagoes of the houseflies lay eggs in the prey, in that the rotary chambers are revolved gradually for a predetermined time period, during which the eggs grow into imagoes and the resulting imagoes fall onto the first nurturing-processing storage unit when the opening of the rotary chamber is directed downwards.

An exemplary embodiment of the invention corresponds mainly to Example 1, the organic fertilizer producing system, characterized in that the larvae discharged out of the last nurturing-processing storage unit are sacrificed and processed as a prey.

Advantages of the Invention

According to an ememplary embodiment of the invention of an organic fertilizer production system, the organic fertilizer base material is produced inside the bodies of larvae of housefly by enzymatic decomposition of excreta of livestock and is excreted out of the larval. Therefore, there is no consumption of fuel which is necessary in case of incineration and an impact on the environment can be reduced, because there is no emotion of carbon dioxide. Still more, unlike the conventional bacterial detoxification, emotion of long-lasting bad smell can be reduced or eliminated and there is no propagation or breeding of pathogens. In the system according to the present invention, excreta are disposed and handled safely by utilizing a preying habit of larvae of houseflies.

Still more, in the system according to an exemplary embodiment of the invention, larvae of houseflies are nourished and nurtured in an enough breeding area and volume with sufficient food. Therefore, the preying habit of larvae of houseflies can be improved and a large amount of excreta of livestock such as swine dung can be changed to organic fertilizer efficiently in a shorter period of time. In particular, in the system according to the present invention, the nurturing-processing storage unit is divided or increased gradually with the progress of growth of larvae, so that prey can be distributed uniformly or evenly.

In addition, the organic fertilizer base material produced by the system according to an exemplary embodiment of the present invention contains abundant chitosan. Such organic fertilizer produced by the system according to the present invention can be used in preparation of organic fertilizer which can improve soil and the antibacterial activity, promote growth of plant, prevent disease of plant, and improve the quality of fruits.

Finally, manual labor in the nurturing-processing storage unit can be reduced so that the organic fertilizer can be produced efficiently with less effort.

According to an exemplary embodiments of the invention of an organic fertilizer production system, in addition to the advantages described above, the edges on roller inflect an abrasion on the skin of larvae of houseflies and the resulting wounded larvae produce much antimicrobial peptides.

According to an exemplary embodiment of the invention of an organic fertilizer production system, in addition to the advantages described above, a part of larvae is grown to imagoes of houseflies which lay eggs, so that reproduction of larvae can be reproduced in the system with no introduction of additional larvae from outside to realize a recycling system of larvae.

According to an exemplary embodiment of the invention of an organic fertilizer production system, in addition to the advantages described above, imagoes of houseflies are guided or induced to a predetermined egg-laying site to improve the efficiency in egg recycling.

According to an exemplary embodiment of the invention of an organic fertilizer production system, in addition to the advantages described above, imagoes of houseflies recovered from the final nurturing-processing storage unit are utilized as excellent prey.

MODE FOR CARRYING OUT THE INVENTION

Figure 1:
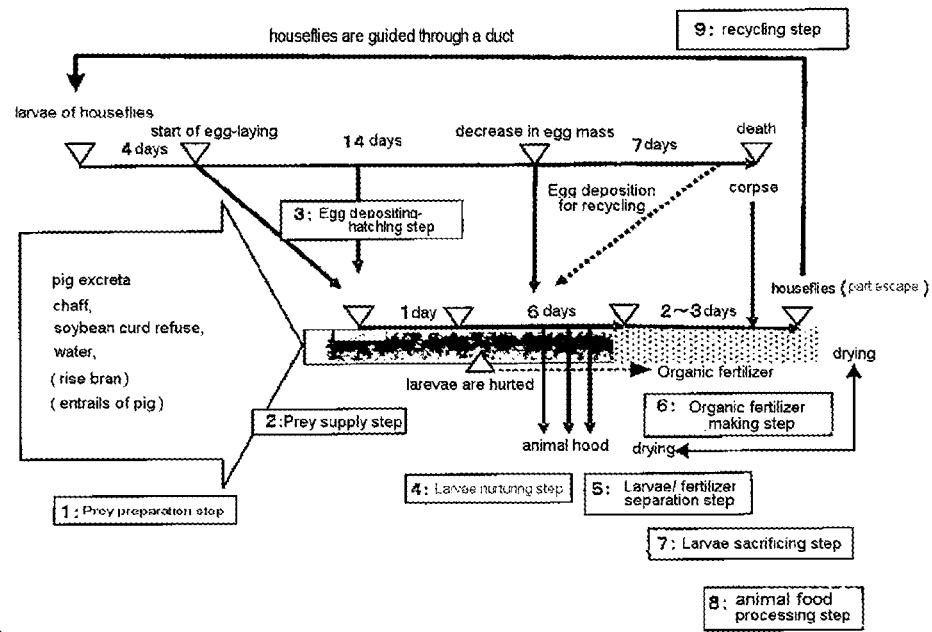
FIG. 1 is a general schematic view of an organic fertilizer production system according to the present invention.

Now, we will describe a general concept of an organic fertilizer production system according to the present invention with reference to FIG. 1.

The organic fertilizer production system of FIG. 1 comprises mainly following steps:
- 1: [Prey preparation step],
- 2: [Prey supply step],
- 3: [Egg depositing-hatching step],
- 4: [Larvae nurturing step],
- 5: [Larvae/fertilizer separation step],
- 6: [Organic fertilizer making step],
- 7: [Larvae sacrificing step],
- 8: [Animal food processing step], and
- 9: [Recycling step]

Outline of each step will be explained below.

1. [Prey Preparation Step]

This prey preparation step is a step for preparing a prey or feed for larvae of *Musca domestica* (housefly) (worms or maggots). The prey is prepared mainly from pig excreta having high nutritional value and is added with chaff, soybean curd refuse, water, rise bran and entrails of pig. In practice, 20 to 40 percents of soybean curd refuse and chaff (about 9:1) is added to pig excreta (or with chicken excreta), the water content is adjusted and mixed together. Food scraps also can be added to the excreta of livestock, so that the food residues are putrefied in excreta to prepare the prey. In fact, food residues are putrefied in excreta to prepare and are changed to prey, so that the system according to the present invention can dispose of a huge volume of human food residues (garbage) together with excreta of livestock.

2. [Prey Supply Step]

In the prey supply step, a predetermined quantity of prey is fed through hoppers which will be explained later in FIGS. 3, 4 onto second to final nurturing-processing storage units arranged in multistage. Respective nurturing-processing storage unit is advanced into a larval nurturing room 2

3. [Egg Depositing-Hatching Step]

In the egg depositing-hatching step, adult larvae are induced into an egg depositing-hatching unit. Housefly can lay eggs 4 days after it becomes an imago but a number of eggs decrease after 14 days. Therefore, the biting medium in the egg depositing-hatching unit is marked with skin milk and sake lees which housefly likes and is irradiated by ultraviolet light to stimulate egg-laying, so that larvae lay eggs at a fixed place. The eggs hatch about one day after egg-laying. The first instar larva is dropped onto the uppermost first nurturing-processing storage unit.

4. [Larvae Nurturing Step]

In the larvae nurturing step, hatched larvae are nurtured in the dark larvae nurturing room 2. The second instar larvae after the first ecdysis are also nurtured in dark or in twilight. The third instar larvae after the second ecdysis but before metamorphosis to pupae are nurtured under light for about 6 days.

Such a habit of larvae of houseflies that they advance themselves for prey is utilized in the present invention. In fact, larvae of houseflies fall themselves down onto next nurturing-processing storage unit and nurtured therein. Then, larvae fall themselves down again to divided next nurturing-processing storage units and nurtured therein.

In case of Example 2, the edges on roller inflect an abrasion on the skin of larvae of houseflies (maggot) when they fall down onto next nurturing-processing storage unit, so that the wounded larvae produce much antimicrobial peptides caused by healing power.

5. [Larvae/Fertilizer Separation Step]

In the larvae/fertilizer separation step, a habit of vermiculation and scattering at a stage of pupa metamorphosis is utilized. The larvae fall down onto a collecting container and are discharged as animal food (E) of high quality. Excretion which is left after the larvae eat excreta of livestock on the nurturing-processing storage unit is conveyed out as organic fertilizer base material.

The separation of the fertilizer from larvae starts from 4th day to 7th day after the egg-deposition. The separation of the fertilizer from larvae can be effected surely by nurturing the third instar larvae under light by utilizing their phototactic behavior at the stage of metamorphosis to pupae.

6. [Organic Fertilizer Making Step]

The organic fertilizer base material is produced during the organic fertilizer making step according to the present invention. In fact, from 65% to 90% of prey is eaten by larvae and remaining prey of from 10% to 35% is fermented. The organic fertilizer base material may be mixed with corpse of larvae of housefly rich in chitosan and cast-off skin of housefly.

7. [Larvae Sacrificing Step],

In the larvae sacrificing step, a group of larvae collected in the collecting container and separated from the organic fertilizer base material is sacrificed by means of steaming, boiling, incineration or the like 4 days after egg-deposition onto prey. Larvae of different insects that may creep in can be excluded in this stage.

8. [Animal Food Processing Step]

In the prey processing step, larvae fall themselves into the collecting container 5 days after egg-deposition onto prey are processed into the animal food (E) like "Trops" (commercial name).

9. [Recycling Step]

In the recycle stage, a part of larvae group is extracted 5 days after egg-deposition onto prey. Then, larvae extracted are brawn to imagoes. The resulting houseflies are induced by light and smell into the egg depositing-hatching unit in [3: egg depositing-hatching step] through the duct due to their habit of phototaxis. The imagoes deposit eggs into prey. Thus, eggs of next generation are obtained or recycled in the system and hence no supply of additional eggs is necessary.

EXAMPLE

Now, we will describe details of the above steps in Example 1 according to the present invention with reference to FIGS. 2-12.

Figure 2:
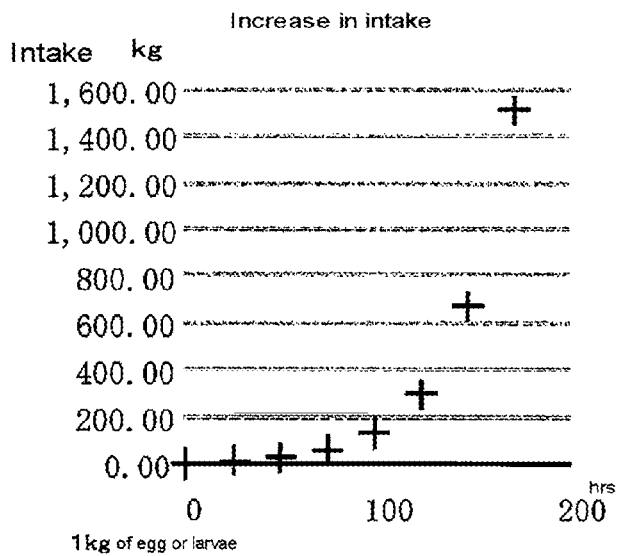
FIG. 2 is a graph showing a change of intake or eating of larvae of houseflies with the progress of their growth.

As stated above, in the system according to the present invention, larvae of housefly can be nurtured in enough larger nurturing volume (area) and sufficient prey can be supplied. FIG. 2 reveals that the intake or eating of larvae of houseflies increase from 1 kg of just after egg-laying to 1600 kg of 7 days after egg-laying if there is a sufficient breeding volume (area) and enough prey. Namely, an amount of eat by larvae of housefly increase 1600 times after 170 hours. This means that such huge amount of excreta like pig feces can be changed by zymolysis within the body of the larvae to excellent organic fertilizer base material.

Such sufficiently larger breeding volume (area) and enough prey for larvae were not available in case of the conventional method in which the larvae are nurtured in the same tray from first to last.

Figure 3:
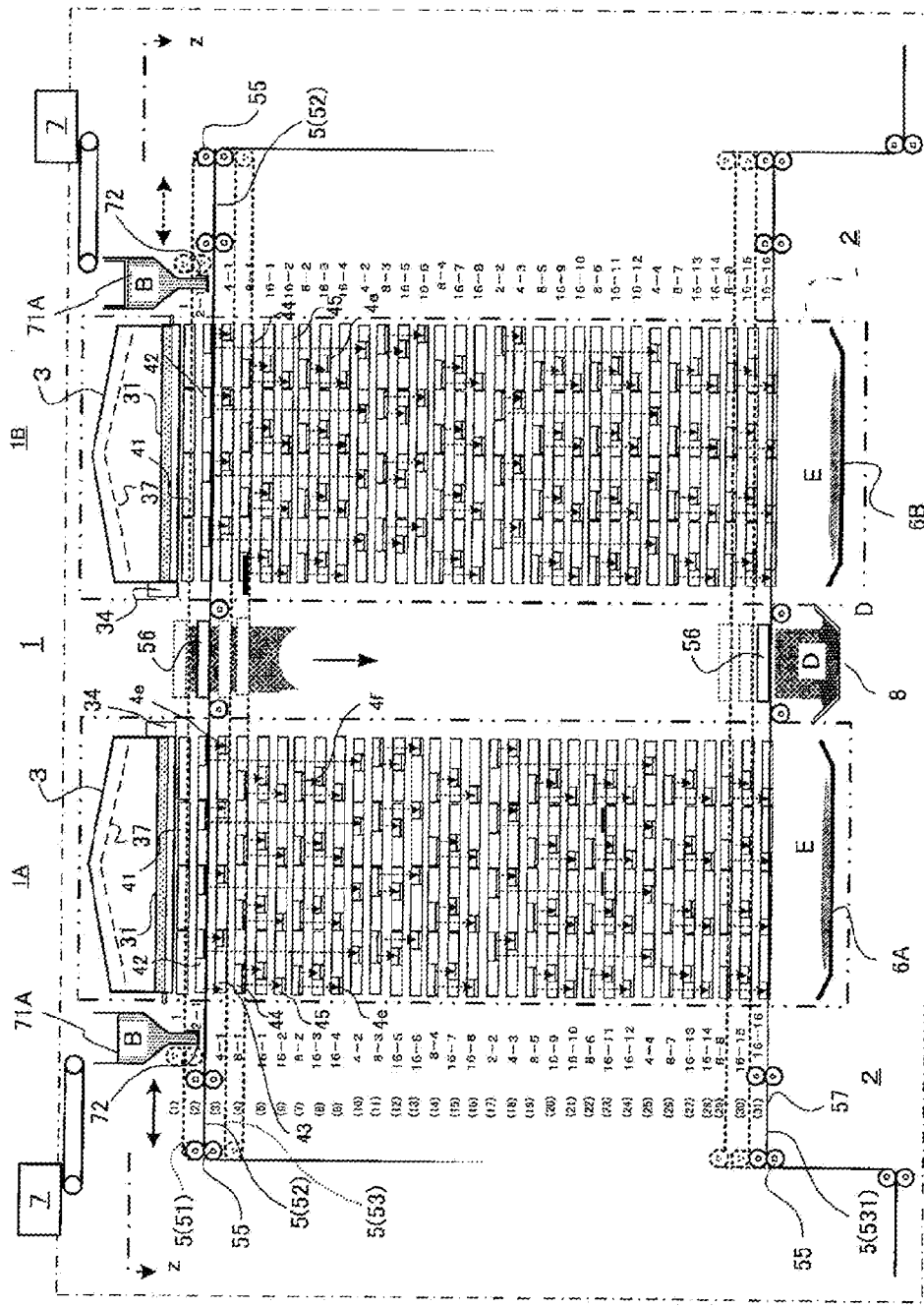
FIG. 3 is an overall illustrative view of an organic fertilizer production system of Example 1 according to the present invention.
Figure 4:
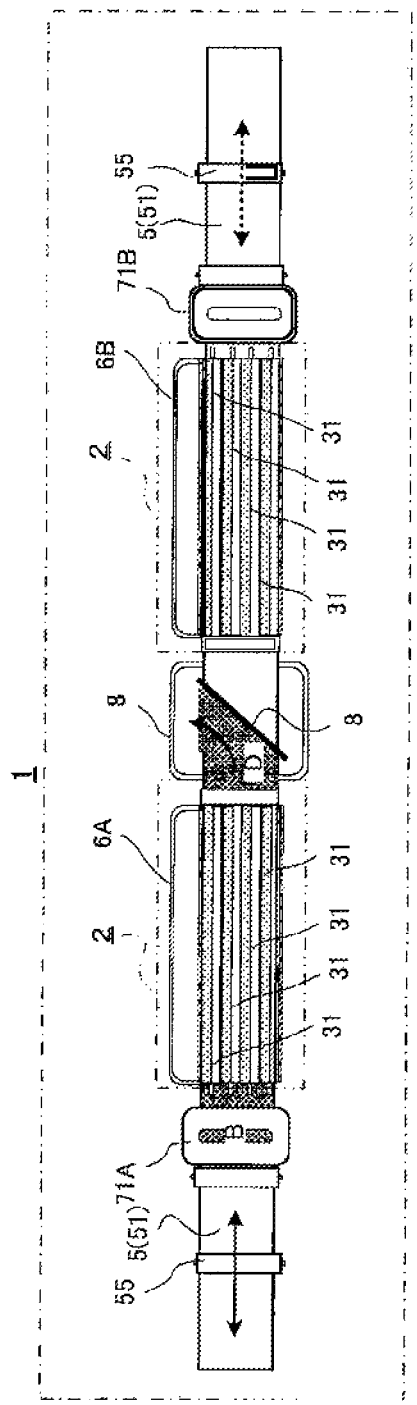
FIG. 4 is a plan view along z-z line in FIG. 3 viewed from the top.

In case of the preset invention, as is shown in FIG. 3 and FIG. 4 (which is sectional plan view along a line of z-z in FIG. 3) which show Example 1, the nurturing-processing storage unit comprise multi-stages (here, 31 levels) and a breeding volume (area) of a lower sage is increased to twice or more than that of an upper stage. Thus, the breeding volume (area) of the nurturing-processing storage units is multiplied successively so that sufficiently larger breeding volume (area) and enough prey are assured for larvae.

(1) [Flow of Egg Deposition]

An installation for producing organic fertilizer shown in FIG. 3 and FIG. 4 has a paired nurturing-processing section (1A) and (1B). Both sections have an almost same structure comprising mainly multi-stag nurturing-processing sections. Therefore, here, one of the towers will be explained with reference to (1A).

The nurturing-processing section (1A) is covered by a larvae nurturing room (2) so that the temperature in a range between 25° C. and 30° C. is maintained and humidity in a range between 50% and 70% is maintained in a nurturing environment. An egg depositing-hatching unit (3) is positioned at the top of the larvae nurturing room (2).

Figure 5:
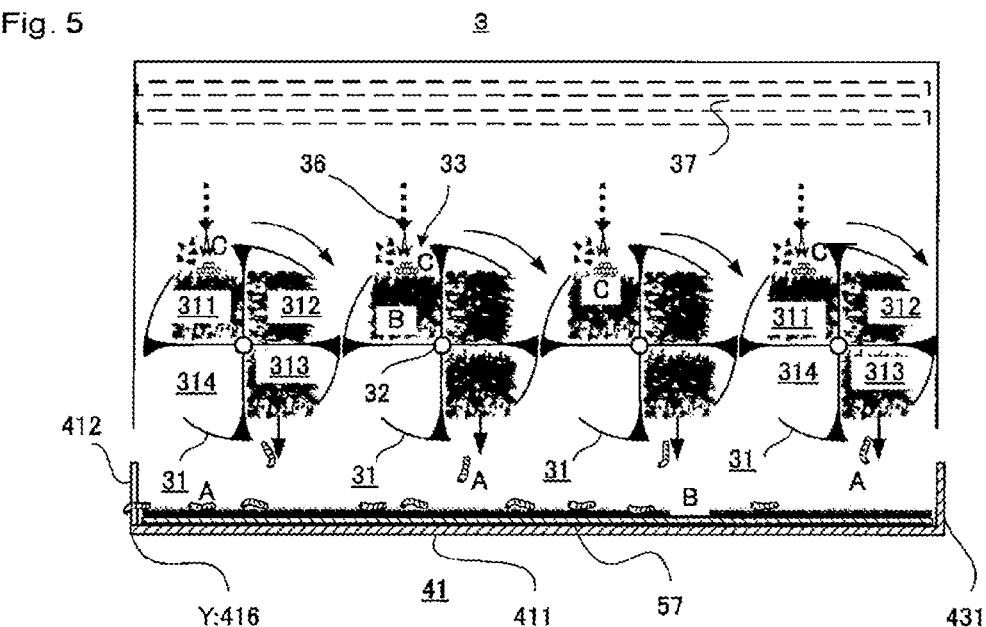
FIG. 5 is a cross-sectional side view of an egg depositing-hatching unit in Example 1.
Figure 6:
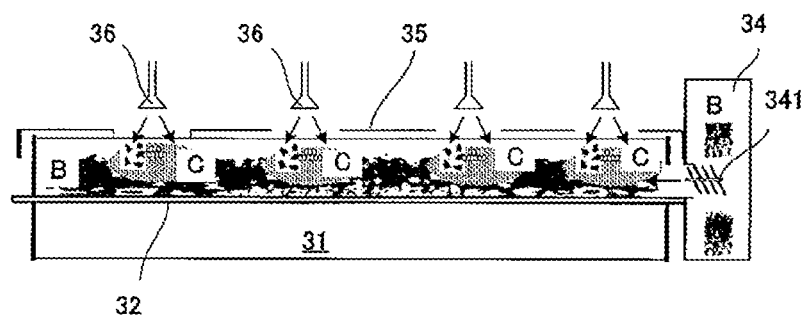
FIG. 6 is a sectional front view of a rotary roller illustrated in FIG. 5.

An egg depositing-hatching unit (3) has four rotary rollers (31) whose shafts are arranged horizontally as shown in FIG. 4 and FIG. 5. Each rotary roller (31) is divided into four chambers as shown in a side cross-sectional view of FIG. 5 and revolves gradually around a rotary shaft (32) at 180 degrees about in a day. Egg and prey are present in the chambers during a period from egg-deposition to hatching. In practice, egg and prey are fed into a first chamber (311), and then the rotary rollers (31) are turned gradually. When second to fourth chambers (312-314) arrive at the position where first chamber (311) had occupied, a prey (B) is fed through a suitable means such as a screw conveyer (341) from a prey supply unit (34).

At a position shown in FIG. 5, a majority of the first chamber (311) along the shaft (32) is covered by a cover (35) and a narrow opening (33) is left. The prey (B) is fed through the opening (33) into the first chamber (311). At the same time, the prey (B) is marked by a marking device (not shown) with an attractive substance consisting of sake lees, skin milk or the like which houseflies like, and ultraviolet rays are irradiated by UV lamps (36) through the opening (33), to attract houseflies by utilizing the habit of adult houseflies.

In fact, houseflies start egg production 4 days after they grow to adult, and the egg production rate will be reduced in 14 days. Therefore, a predetermined location or the opening (33) is marked during this period to attract houseflies and to induce their egg-laying.

A perching net (37) is hung up near a ceiling of the egg depositing-hatching unit (3) so that houseflies can rest during fee flying time other than egg-deposition time.

Eggs are laid in the first chamber (311) as an egg-laying room shown in FIG. 5. In this time, hatching already started in the second chamber (312) in which egg-laying has been finished in the previous stage and then had turned about 90 degrees. And, in the third chamber (313) which had turn further 90 degrees, the opening (33) is directed downward, so that hatched larvae (A) and remaining prey (B) fall onto the first nurturing-processing storage unit (41). The fourth chamber (314) rotated further 90 degrees is now empty and is ready to become next egg-laying chamber.

In summary, the egg depositing-hatching unit (3) in the egg depositing-hatching section has a plurality of first to fourth rotatable chambers, a prey (B) is fed into a chamber whose opening is directed upwards, and the prey (B) is irradiated with ultraviolet light to attract imagoes of houseflies and to induce their egg-deposition. These first to fourth chambers are turned gradually or stepwise, during which the eggs grow to larvae. The resulting larvae fall through the opening directed downwards onto the first nurturing-processing storage unit.

(2) [Flow of Larvae]

The first nurturing-processing storage unit (41) in the nurturing-processing sections 1A is an uppermost one of nurturing-processing storage units (4) which are sucked in (31) multi-levels and arranged in 4 rows.

Figure 7:
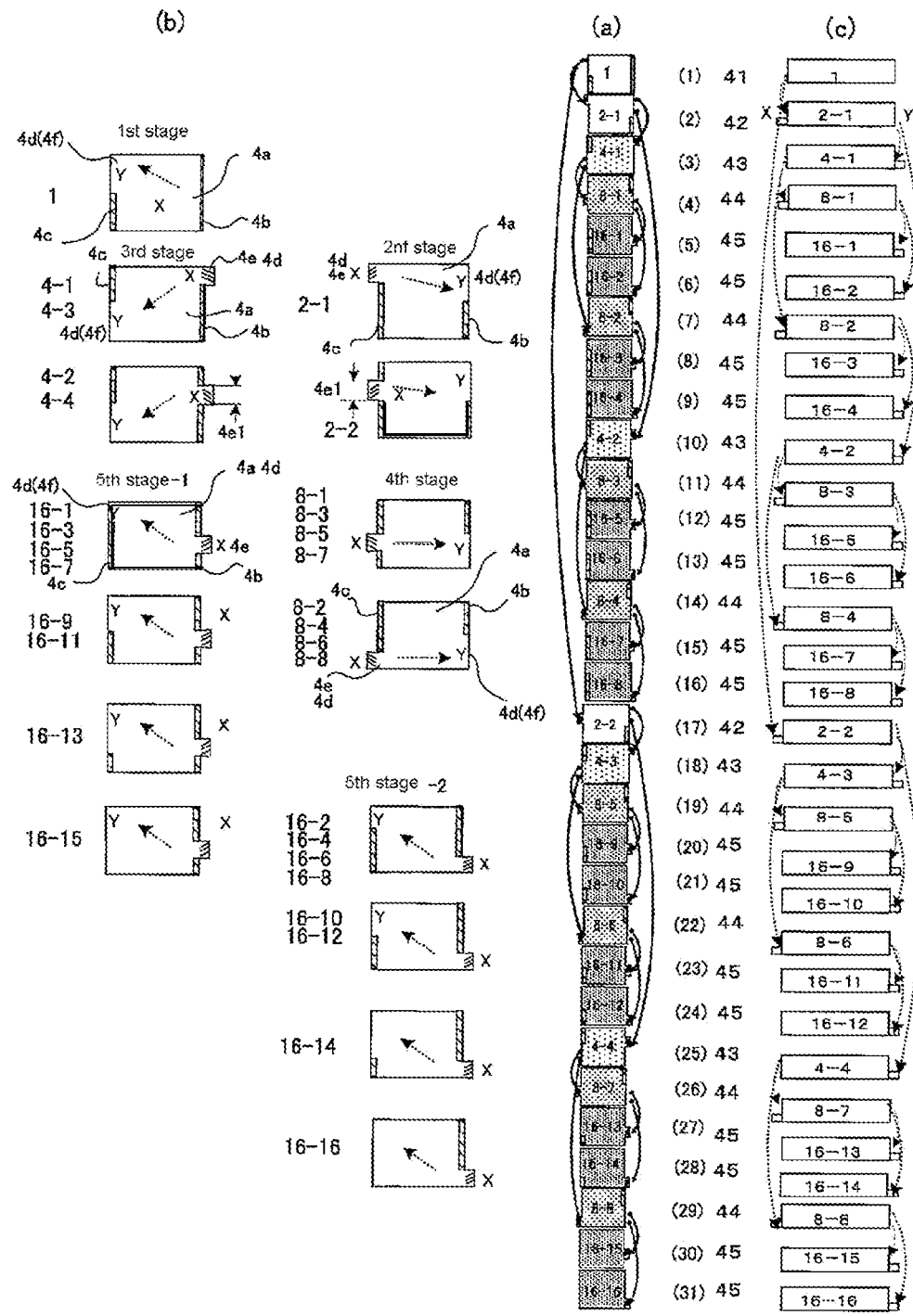
FIG. 7(*a*) is a development of nurturing-processing storage units of FIG. 3, FIG. 7(*b*) illustrates enlarged views of the nurturing-processing storage units of FIG. 7(*a*) and FIG. 7(*c*) is a side view of one of the nurturing-processing storage units of FIG. 3.
Figure 8:
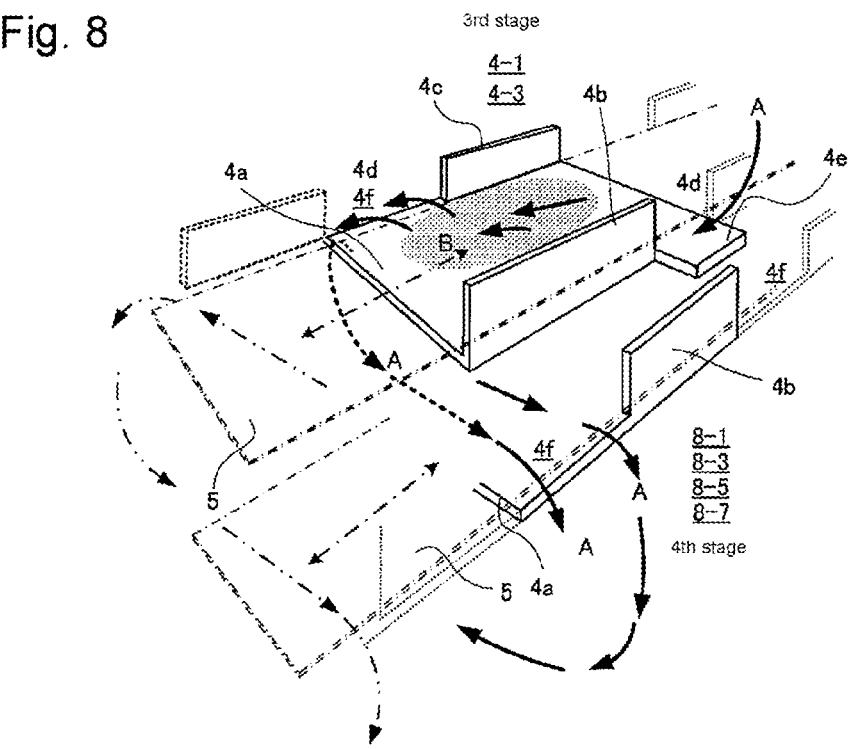
FIG. 8 is an enlarged perspective view of the nurturing-processing storage unit.

Now, the entirety of the nurturing-processing storage units (4) will be explained with refereeing to FIG. 3 to FIG. 8. FIG. 4 is a plain view of FIG. 3. FIG. 7 is a development of each nurturing-processing storage unit (4). FIG. 8 is an enlarged perspective view of the third stage (4-1) and fourth stage (8-1).

FIG. 7(a) is a development of the nurturing-processing storage unit (4) of FIG. 3. FIG. 7(b) is an illustrative enlarged plain view of the nurturing-processing storage unit of FIG. 3. FIG. 7(c) is an illustrative side view of one of the nurturing-processing storage units of FIG. 3.

In more precisely, FIG. 7(a) is a series of developments of plain views of all stages of the nurturing-processing storage units (4) stacked in 31 levels in FIG. 3. Numbers such as (1) (2) (3)—denote stage numbers from the top and, while signs of 1, 2-1, 4-1—described in each storage unit denote increment in stages. For example, 1: First stag nurturing-processing storage unit (41).

2-1: First storage unit of the second stage nurturing-processing storage unit (42). Now, the total volume of the nurturing-processing storage units is doubled.

2-2: Second storage unit of the second stage nurturing-processing storage unit (42), 4-1: First storage unit of third stage nurturing-processing storage unit (43). Now, the total volume of the nurturing-processing storage units is further doubled or quadrupled in total.

8-1: First storage unit of fourth stage nurturing-processing storage unit (44). Now, the total volume of the nurturing-processing storage units is further doubled or increased to 8 times in total.

16-1: First storage unit of fifth stage or final nurturing-processing storage unit (45). Now, the total volume of the nurturing-processing storage units is further doubled or increased to 16 times in total.

In FIG. 7(b), "X" denotes a location or position of a receiving part, "Y" denotes a location or position of a dropping part, a hatched area denotes a side wall, and an arrow shows a direction along which larvae craw advance.

Now, we will be described the nurturing-processing storage unit much in details with reference to FIG. 8 which is an enlarged perspective view of an example of the nurturing-processing storage unit.

FIG. 8 shows third nurturing-processing storage unit (43) (4-1) of the third stage and another nurturing-processing storage unit (44) (8-1) positioned below shown in FIG. 3.

Third stage nurturing-processing storage unit (43) (4-1) has a bottom part (4a) and opposite side walls (4b) (4c) and has a substantially U-shaped cross section. The nurturing-processing storage unit (4) is secured to a frame of the larvae nurturing room (2) but can be, of course, supported movably on wheels if necessary.

A notched part (4d) is formed on one (4b) of the side walls (a wall on a front side in FIG. 8). At a position of the notch part (4d), the bottom part (4a) projects outwards to form a flat extension part (index-type) which functions as a receiving part (4e). A width (4d1) of the notched part (4d) is about ¼ of the total length of the side wall. Larvae (A) of houseflies falling down from above are received by the receiving part (4e) and are induced to the prey (B) which is spread all over a flat body 5 (53) arranged on the bottom part (4a).

The flat body 5 (53) arranged on the bottom part (4a) in FIG. 8 is a belt of stainless steel and is guided reciprocally along the side walls (4b)(4c). In practice, the flat body 5 (53) slides on the bottom part (4a) and is covered with the prey (B) which is spread uniformly over an upper surface of the flat body (5) (53).

Another notched part (4f) is formed on another (4c) of the side walls (a wall on a backward in FIG. 8) so that larvae enable to drop down. A width of the notched part (4f) is about ½ of the total length of the side wall (4c). The larva (A) crawling and searching for the prey (B) on the flat body (5) (53) fall down onto respective receiving parts of lower two nurturing-processing storage units (8-1, 8-2) arranged at fourth level and seventh level respectively. Each of these receiving parts has a width of about ¼ of the total length of the side walls (4b) (4c).

The other nurturing-processing storage units (4) also have the same structure as those explained for the third stage nurturing-processing storage unit (43). In fact, as can be seen from the development view of FIG. 7, larvae dropping from the first nurturing-processing storage unit (41) fall down onto lower two nurturing-processing storage units (42) with two separate groups, one group falls onto the second stage nurturing-processing storage unit arranged at second level (2-2) and another group fall onto the second stage nurturing-processing storage unit arranged seventeenth level (2-2).

Then, respective groups fall down onto further lower two nurturing-processing storage units (43) again with two separate groups. Now, a number of the nurturing-processing storage units increase to 4, namely, the third stage nurturing-processing storage unit arranged at third level (4-1), tenth level (4-2), eighteenth level (4-3) and twenty-fifth levels (44).

Then, respective groups fall down onto further lower two nurturing-processing storage units (44) again with two separate groups. Now, a number of the nurturing-processing storage units increase to 8, namely, the fourth stage nurturing-processing storage unit arranged at fourth level (8-1), seventh level (8-2), eleventh level (8-3), fourteenth level (8-4), nineteenth level (8-5), twenty-second level (8-6), twenty-six level (8-7) and twenty-ninth level (8-8).

Then finally, respective groups fall down onto further lower two nurturing-processing storage units (45) again with two separate groups. Now, a number of the nurturing-processing storage units increase to 16, namely, the fifth stage nurturing-processing storage unit arranged at fifth level (16-1), six level (16-2), eighth level (16-3), ninth level (16-4), twentieth level (16-5), thirteenth level (16-6), fifteenth level (16-7), sixteenth level (16-8), twenty level (16-9), twenty-first level (16-10), twenty-third level (16-11), twenty-fourth level (16-12), twenty-seventh level (16-13), twenty-eight level (16-14), thirtieth level (16-15) and thirty first level (16-16).

Namely, start from the first one nurturing-processing storage unit (41), a number of the nurturing-processing storage units is multiplied by two ("2") and increased finally to seventeen units in the final nurturing-processing storage units (45).

In this case, as shown in FIG. 8, larvae (A) of houseflies across the nurturing-processing storage unit (4) transversely in each stage, and then change their traveling direction in following nurturing-processing storage unit (4). In other words, they travel transversely a plurality of nurturing-processing storage units (4) along opposite direction successively.

This structure of the present invention is advantageous to save a space, although stacked nurturing-processing storage units (4) become a tall tower. Alternatively, a lower stage for example the second stage can be constructed by two parallel rows of the nurturing-processing storage units. In this case, freedom in designing of the width of the dropping part increase and a height of the tower can be reduced to a half but an area occupied by the nurturing-processing storage units (4) becomes double.

Thus, a plurality of receiving parts are formed on a lower nurturing-processing storage unit (4) for receiving falling larvae from an upper nurturing-processing storage unit (4), a width of the receiving part being equal to a value which is a corresponding width (4f) of the dropping part of the upper nurturing-processing storage unit (4) divided by a number of lower nurturing-processing storage units (4). Enough nurturing volume for larvae is assured by increasing the nurturing-processing storage units (4) to a predetermined number, and hence the nurturing-processing storage unit can be supplied with sufficient amount of prey, so that eating habit of larvae can be promoted.

In this Example, the system according to the present invention is designed such that a period from egg-laying to a time when larvae fall from the final nurturing-processing storage unit (45) will be about 6 to 7 days. Generally, the system according to the present invention can be realized by designing a volume of each nurturing-processing storage unit (4) through which larvae travel and/or by setting the number of nurturing-processing storage unit (4) and the number of their stages.

Here, movement of larvae in the nurturing-processing storage unit (4) as well as their flow is explained in much in details. When the four rotary rollers (31) in the egg depositing-hatching unit (3) rotate, hatched larvae (A) of houseflies fall from each chamber (311-3149 of the rotary roller (31) onto the first nurturing-processing storage unit storage unit (41). In case of the first nurturing-processing storage unit storage unit (41), an upper surface of its bottom part (a) forms the flat boy (51) and functions as a receiving part. In other words, unlike the receiving part of other nurturing-processing storage units, this flat boy (51) itself forms the receiving part (4e) but has not the flat extension part. The larvae eat prey (B) spread over the flat boy (51) and advance toward the fall part (40. The larvae arrived at the fall part (4f) fall onto the receiving part of (4e) of lower second nurturing-processing storage uniting storage unit (42) with such a manner that the larvae are divided into two groups each falls onto each receiving part of (4e) of the second nurturing-processing storage uniting storage unit (2-1, 2-2).

The larvae continue to grow in similar manner in the third nurturing-processing storage uniting (43) and nurturing-processing storage unit (44) whose number is increased by at a multiple of 2. After prey on the final nurturing-processing storage unit (45) is exhausted by the larvae, the larvae crowd at the fall par (4f) and fall onto a larvae collecting section (6A, 6B) which is a collecting container having a larger area than the final nurturing-processing storage unit (45).

Larvae collected in a collecting container arranged in the larvae collecting section (6A) are remained in this section for more than 5 days. Then, the collecting container contained the larvae is withdrawn out of the larvae nurturing room (2) under died condition.

A part of larval group is extracted and grown into adults. The resulting adult houseflies are guided or induced into the egg depositing-hatching unit (3) through a duct (not shown) by utilizing their habit of phototaxis and runnability for light and smell. Thus, houseflies are recycled.

Remaining group of larvae (A) that is not extracted in the larval collecting part (6A) is sacrificed by steaming, boiling, incineration or the like. The resulting product can be an animal food (E) of good quality rich in chitosan and is shipped after predetermined processing.

(3) [Flow of Livestock Excreta]

Now, a flow of livestock excreta is explained. In this Example, a prey or a food for larvae of houseflies or is prepared in a prey preparation unit (7). In this unit (7), soybean curd refuse and chaff (about 9:1) is added to pig excreta (chicken excreta) at a proportion of 20 to 40%, the water content is adjusted and mixed together. Food scraps also can be added to the excreta of livestock, so that the food residues are putrefied in excreta to prepare the prey. In fact, since food residues are putrefied in excreta to prepare and are changed to prey, the system according to the present invention can dispose of a huge volume of human food residues (garbage) together with excreta of livestock.

The resulting prey is fed to a prey supply section from which a predetermined amount of the prey (B) is conveyed to a prey supply hoppers (71A) (72B) of FIGS. 3. 4. The prey (B) is spread uniformly onto an upper surface of the flat body (5, 51, 52-531) through a prey control gate (72) of the prey supply hoppers (71A) (72B). The flat body (5, 51, 52-531) of the nurturing-processing section (1A) is moved to the right in FIG. 3 by a prey roller (55) driven by a motor (not shown). The flat body (5, 51, 52-531) can be a belt conveyor. Advancing velocity of the flat body (5, 51, 52-531) and opening and closing of the gate (72) are controlled in such a manner that the prey (B) presents on a surface of the flat body (5, 51, 52-531) located in the nurturing-processing storage unit (4).

Interior of the larvae nurturing room (2) is maintained at a temperature of 25 to 30° C. and a humidity of from 50% to 70%.

After or during the prey is supplied uniformly on the flat body (5, 51, 52-531), the flat body (5, 51, 52-531) is advanced into the larvae nurturing room (2) and stops therein. Hatched larvae are nurtured in the dark larvae nurturing room (2). The second instar larvae after the first ecdysis are also nurtured in dark or in twilight. The third instar larvae after the second ecdysis but before metamorphosis to pupae are nurtured under light for about 6 days. During the nurturing and breeding, larvae eat the prey in the nurturing-processing storage unit (4) and the prey is decomposed enzymatically within the larvae and excreted to produce the organic fertilizer base material Almost all prey (B) composed of excreta of livestock etc. on the flat body (5, 51, 52-531) in the nurturing-processing storage unit (4) is treated by enzymatic decomposition within the body of larvae (A) and is excreted as the organic fertilizer base material (D).

Usually, from 65% to 90% of prey is eaten by larvae and remaining prey of from 10% to 35% is fermented, so that resulting products provide the objective organic fertilizer base material (D). In practice, the above products are mixed with corpse of larvae of housefly rich in chitosan and with cast-off skin of housefly to produce the final organic fertilizer base material (D).

The flat body (5, 51, 52-531) on which a product of organic fertilizer base material (D) is stocked is then moved again (to the right in FIG. 4), so that the organic fertilizer base material (D) is pushed out from the flat body (5, 51, 52-531) by means of a scraper (56) secured to the larvae nurturing room (2) so that the organic fertilizer base material (D) is turned at 90 degree and is dropped into a collecting container in an organic fertilizer base material collecting section (8) located at the base of the larvae nurturing room (2). During the fall, the organic fertilizer base material (D) is died. Finally, the collecting container containing the dried organic fertilizer base material (D) is withdrawn from the larvae nurturing room (2) for shipping.

As explained above, the organic fertilizer production system shown in Example 1 according to the present invention repeats a cycle comprising (1) [Flow of egg deposition], (2) [Flow of larvae] and (3) [Flow of livestock excreta] for about one week to produce organic fertilizer base material repeatedly and automatically.

In the organic fertilizer production system of Example 1, the organic fertilizer base material is produced within the bodies of larvae of housefly enzymatic decomposition of excreta of livestock and excreted out of the larval. Therefore, there is no consumption of fuel which is necessary in case of incineration and an impact on the environment can be reduced, because there is no emotion of carbon dioxide. Still more, unlike the conventional bacterial detoxification, emission of long-lasting bad smell can be reduced or eliminated and there is no propagation or breeding of pathogens. In the system according to the present invention, excreta are disposed and handled safely by utilizing a preying habit of larvae of houseflies.

Still more, in the organic fertilizer production system of Example 1, there are 31 levels of the nurturing-processing storage units, so that larvae of houseflies are nourished and nurtured in an enough breeding area and volume with sufficient food. Therefore, large amount of excreta of livestock such as swine dung can be changed a large amount of excreta of livestock such as swine dung to organic fertilizer efficiently in a shorter period of time. In particular, the nurturing-processing storage section is divided into 31 nurturing-processing storage units, so that prey can be distributed uniformly or evenly with the progress of growth of larvae.

In addition, the organic fertilizer base material produced by the system according to the present invention contains abundant chitosan. Such organic fertilizer produced by the system according to the present invention can be used in preparation of organic fertilizer which can improve soil and the antibacterial activity, promote growth of plant, prevent disease of plant, and improve the quality of fruits. Finally, manual labor in the nurturing-processing storage unit can be reduced, so that the organic fertilizer can be produced efficiently with less effort.

Since a part of larvae group or of pupas is extracted and is brawn to imagoes and the resulting imagoes deposit eggs into prey, eggs of next generation are obtained or recycled in the system and hence no supply of additional eggs is necessary.

The larvae discharged from the final nurturing-processing storage unit can be used as animal food (E) of good quality rich in chitosan.

Example 2

Example 2 is explained with reference to FIG. 9. A structure of Example 2 is same as Example 1 except a structure of the receiving part. Therefore, their details are not explained here.

In Example 2, whole or part of the extension part (4e) projected outwardly from the flat body (index-type) is replaced by an edged part (46) of an edged roller (461).

Figure 9:
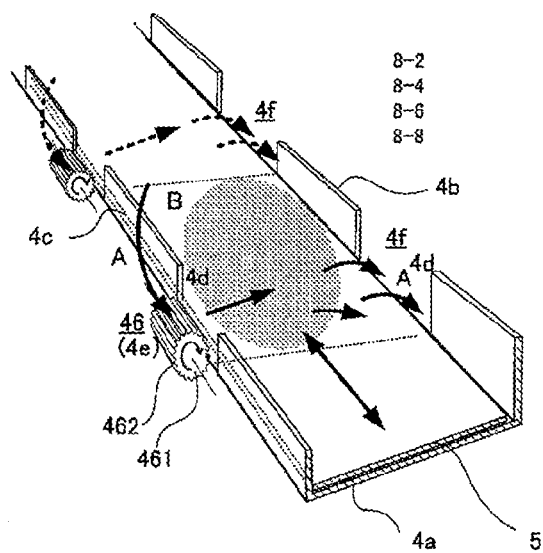
FIG. 9 is an enlarged perspective view of a roller-type receiving part used in Example 2 according to the present invention.

As shown in FIG. 9, a lower nurturing-processing storage units (4) has an edged roller (461) having an edged part (46) to inflect an abrasion on the skin of larvae of houseflies. A width of the edged part (46) is equal to a corresponding width (4f) of the dropping part of an upper nurturing-processing storage unit (4) divided by a suitable number.

It is known that the wounded larvae produce much antimicrobial peptides caused by healing power. To use this fact, in this Example, the parts (46) of the edged roller (461) inflect an abrasion on the skin of larvae of houseflies when they move and fall down onto next nurturing-processing storage unit.

The edged roller (461) can be positioned at a desired receiving part (4e) where the larvae produce much antimicrobial peptides and can extend whole or part of the receiving part.

Other functions and advantages of Example 2 are same as Example 1.

Example 3

Figure 10:
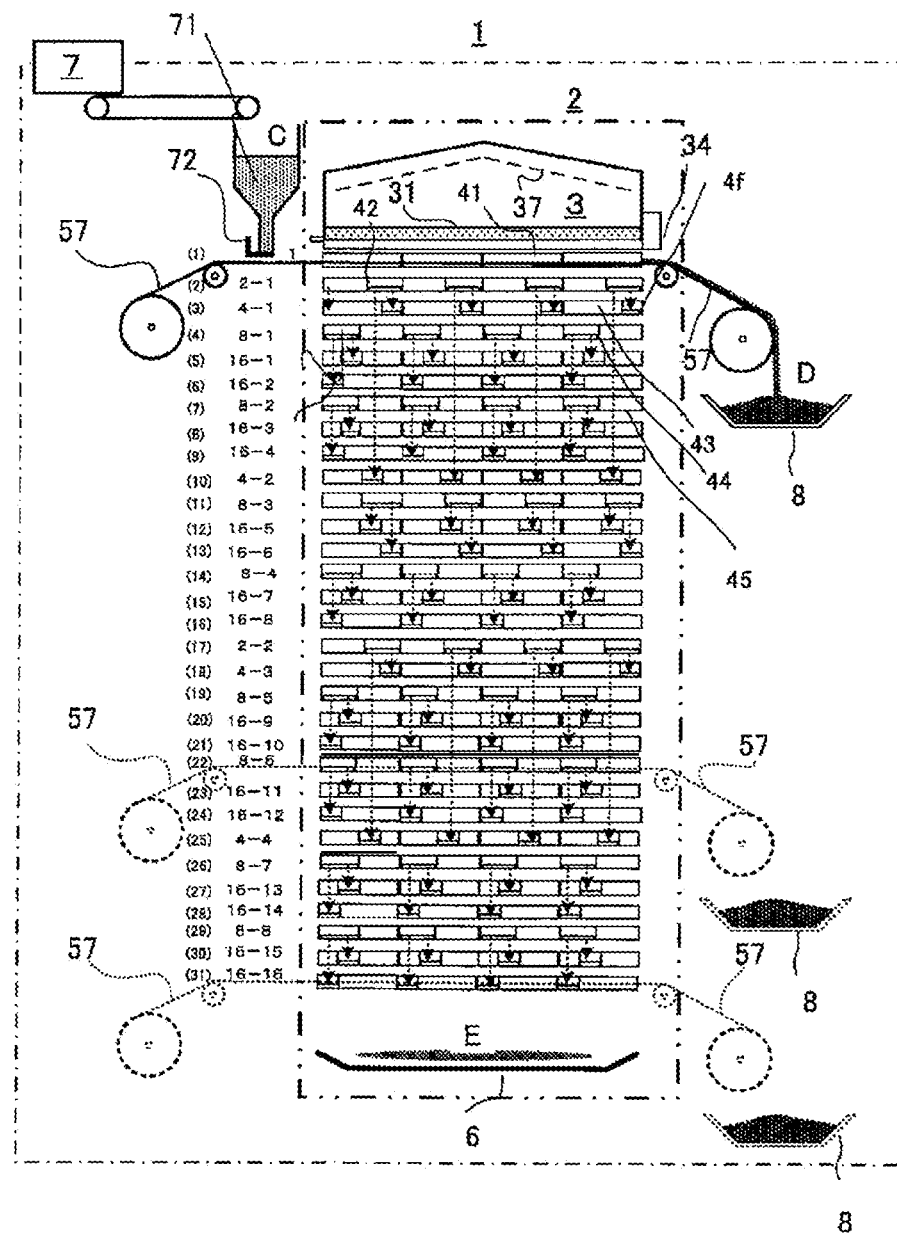
FIG. 10 is an overall illustrative view of an organic fertilizer production system of Example 3 according to the present invention.

Example 3 is described with reference to FIG. 10. A structure of Example 3 is same as Example 1, as shown in FIG. 10, but the reciprocating flat body (5) made of stainless steel in Example 1 is replaced by a continuous plastic film (57) which advices unidirectionally and wound up. Still more, a single nurturing-processing section (1) is used instead of paired nurturing-processing section (1) in Example 1. Other structures of Example 3 are same as Example 1 and hence their details are not explained here.

The structure of Example 3 is simplified in comparison with Example 1 in which the flat body (5, 51, 52-531) is reciprocated but cleaning of continuous plastic film (57) is required for its reuse.

Example 3 has such merits in comparison with Example 1 that the plant can be compact owing to use of a single nurturing-processing section (1) and of a continuous plastic film (57).

Example 4

Example 4 is described with reference to FIG. 11.

In Example 1, starting the first one nurturing-processing storage unit (41), a number of nurturing-processing storage units are increased with the multiplier of "2" and the final number of nurturing-processing storage units (45) becomes 16. While a number of nurturing-processing storage units (4) are increased with a multiplier of "3", a number of nurturing-processing storage units (4) are increased with the multiplier of "3". Example 4 shows this case.

Figure 11:
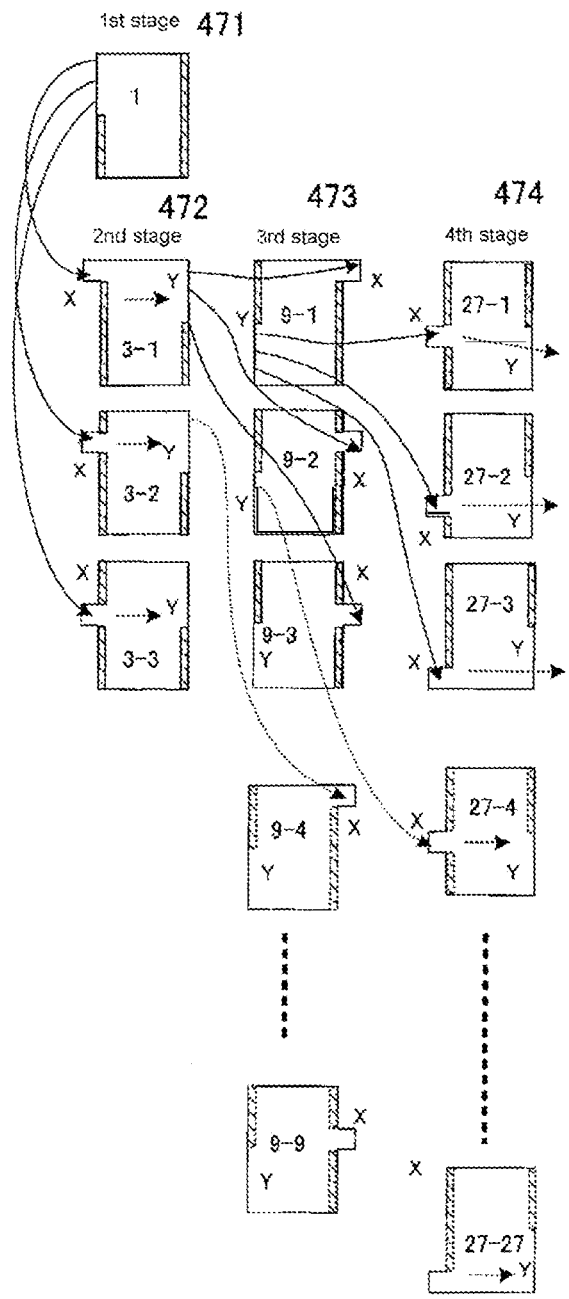
FIG. 11 is a development of nurturing-processing storage units of Example 4 according to the present invention.

As shown in FIG. 11, the first nurturing-processing storage unit (471) has a drop part (Y) and following second stage is increased into three nurturing-processing storage units (472). Each second stage nurturing-processing storage unit (472) has a receiving part (X) whose width is ⅓ of the width of the drop part (Y) of the first nurturing-processing storage unit (471). Similarly, three nurturing-processing storage units (473) are used for each of the second stage nurturing-processing storage unit (472). Each third stage nurturing-processing storage unit (473) has a receiving part (X) whose width is ⅓ of the width of the drop part (Y) of the second nurturing-processing storage unit (472). This is repeated also in the final fourth stage nurturing-processing storage unit (474). As a result, a number of nurturing-processing storage units (4) are increased with the multiplier of "3" and the total area of the final stage nurturing-processing storage units (45) is increased to 27 times (1×3×3×3).

The degree of increment of the nurturing-processing storage units can be adjusted to the progress of growth of larvae, by designing and selecting appropriate number of divisions in each stage nurturing-processing storage unit by using the dividing method of Example 1 and Example 4 or other similar dividing method.

The width of the receiving part of Example 4 is narrower than that of Example 1. In this case, an area of lower nurturing-processing storage unit may be increased.

Similarly, a number of nurturing-processing storage units can be increased with the multiplier of "4". In this case, four nurturing-processing storage units (472) are used in the second stage for one nurturing-processing storage units (471). Each second stage nurturing-processing storage unit (472) has a receiving part (X) whose width is ¼ of the width of the drop part (Y) of the first nurturing-processing storage unit (471).

Example 5

Example 5 is explained with reference to FIG. 12.

In Example 1 and Example 5, the drop part and the receiving part of the nurturing-processing storage units (4) are fixed, while the flat body is moved on an upper side of the bottom part.

Figure 12:
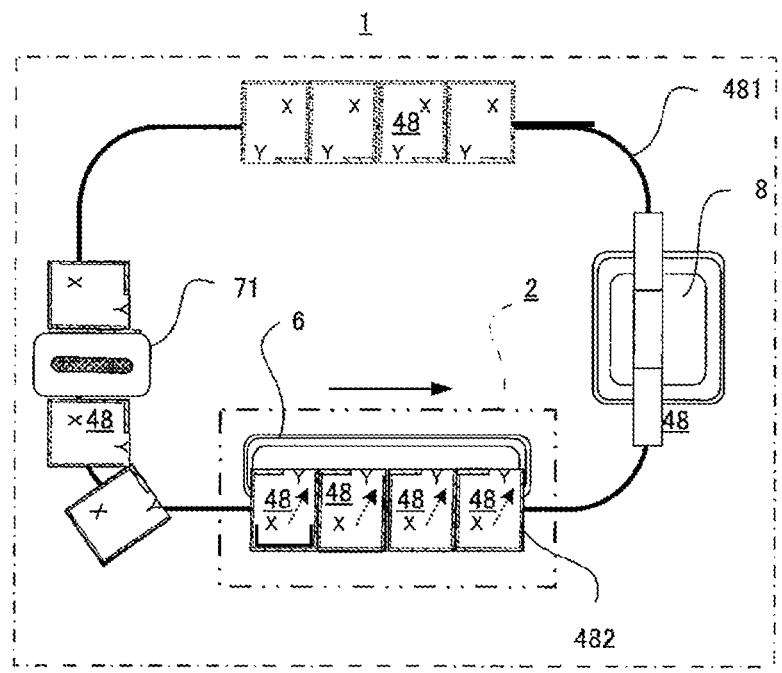
FIG. 12 is an overall illustrative view of an organic fertilizer production system of Example 5 according to the present invention.

In Example 5, the nurturing-processing storage units (4) used in Example 1 and Example 5 are constructed in a form of a movable container type (trays), so that a plurality of nurturing-processing storage units (4) themselves are displaced, as is shown in FIG. 12. Thus, a plurality of movable container type nurturing-processing storage units (4) is traveled by a loop conveyor (482). The nurturing-processing storage unit (4) has a form of a tray comprising the dropping part, the receiving part, the bottom part and partitions (481) separating a volume of the tray into a plurality sections along its longitudinal direction.

As shown in FIG. 12, the trays (48) mounted on the loop conveyor (482) are supplied with a predetermined amount of prey (B) such as livestock excreta from a hopper (71). Then, the trays (48) are advanced to the larval larvae nurturing room (2) in which larvae are supplied from the egg depositing-hatching unit (3) (see FIGS. 5, 6) arranged at the top of the larvae nurturing room (2) in the same manner as in Example 1. Trays are stacked in multi levels in the same manner as in Example 1, larvae eat the prey, crawl advance, fall onto lower tray (48) by themselves and finally are collected in the larvae collecting section (6).

The tray (48) filled with organic fertilizer base material (D) which is an excreta of larvae is advanced from the larvae nurturing room (2) to the organic fertilizer base material collecting section (8). The organic fertilizer base material (D) is discharged from the trays (48) into a container by tilting or turning the trays. Other structure, functions and advantages are basically same as in Example 1 and are not described repeatedly.

Note that the present invention is not limited to above Examples as a matter of course, but can modify freely unless impair the characteristics of the present invention.

REFERENCE NUMBER

A larvae,
B prey,
C egg,
D organic fertilizer base material,
E animal food,
1, 1A, 1B nurturing-processing section,
2 larvae nurturing room,
3 egg depositing-hatching unit,
31 rotary rollers,
311 1st chamber,
312 2nd chamber,
313 3rd chamber,
314 4th chamber,
32 rotating shaft
33 opening part,
34 prey supply unit,
341 screw conveyer,
35 cover,
36 UV lamp,
37 perching net,
4 nurturing-processing storage unit,
4a bottom part,
4b, 4c side wall,
4d notched part,
4e receiving part (X: flat body: index type),
4e1 width,
4f dropping part (Y),
41,471 1st nurturing-processing storage unit,
42,472 2nd nurturing-processing storage unit,
43,473 3rd nurturing-processing storage unit,
44,474 4th nurturing-processing storage unit,
45 final nurturing-processing storage unit,
46 receiving part (X: roller type),
461 edged roller,
462 edges,
48 tray (mobile container type nurturing-processing storage unit),
481 partitions
482 loop conveyer,
5, 51, 52-531 flat body
55 feed roller,
56 scraper,
57 flat body (elongated film),
6, 6A, 6B larvae collecting section,
7 prey preparation unit,
71, 71A, 71B prey supply hopper,
72 gate,
8 organic fertilizer base material collecting section

The invention claimed is:

1. An organic fertilizer producing system for producing organic fertilizer from excreta of livestock or domestic animal by using larvae of *Musca domestica* (housefly), comprising,
a first nurturing-processing storage unit for nurturing or growing larvae hatched from eggs,
a plurality of second nurturing-processing storage units are arranged below the first nurturing-processing storage unit,
wherein said first nurturing-processing storage unit has a dropping part, so that grown larvae drop onto said second nurturing-processing storage units covered with excreta of livestock, by utilizing such a behavior of larvae that they crawl out of said first nurturing-processing storage unit,
a plurality of third nurturing-processing storage units are arranged below the second nurturing-processing storage units in the same way as above, so that grown larvae drop onto said third nurturing-processing storage units covered with excreta of livestock,
wherein said excreta of livestock are decomposed with enzyme within larvae bodies while larvae are nurtured in each nurturing-processing storage unit, while the larvae excrete or produce an organic fertilizer base material,
a collecting section for collecting the produced organic fertilizer base material,
a larvae collecting section for collecting grown larvae crawling out of a final nurturing-processing storage unit, the resulting collected larvae as well as the produced organic fertilizer base material being carried out of the system, and
said larvae collecting section has an imago extraction part for extracting a part of imagoes or a part of pupas grown, so that imagoes of houseflies extracted in said imago extraction part are guided through a duct to an egg depositing-hatching unit located above said first nurturing-processing storage unit.

2. The organic fertilizer producing system according to claim 1, wherein each of said nurturing-processing storage units comprises a dropping part and a receiving part for larvae on a fixed frame, and a bottom part on which a moveable flat body is placed.

3. The organic fertilizer producing system according to claim 1, wherein each of said nurturing-processing storage unit has a receiving part located at a position corresponding to said dropping part of an upper nurturing-processing storage unit, said receiving part comprising a flat body in a form of a projection which projects outward and having a width equal to a width of said dropping part divided by a predetermined number.

4. The organic fertilizer producing system according to claim 1, further comprising a plurality of rotary chambers arranged in said egg depositing-hatching unit and a prey is fed into one of said chambers whose opening is directed upwards, while said prey is irradiated with ultraviolet rays, so that larvae of the houseflies lay eggs in the prey, in that said rotary chambers are revolved gradually for a predetermined time period, during which the eggs grow into larvae and the resulting larvae fall onto said first nurturing-processing storage unit when said opening of the rotary chamber is directed downwards.

5. The organic fertilizer producing system according to claim 1, wherein said larvae discharged out of the final nurturing-processing storage unit are sacrificed and processed into animal food.

* * * * *